US006927035B1

(12) United States Patent
Soma

(10) Patent No.: US 6,927,035 B1
(45) Date of Patent: Aug. 9, 2005

(54) ANTIURACIL MONOCLONAL ANTIBODY

(75) Inventor: Gen-ichiro Soma, Tokyo (JP)

(73) Assignees: Taiho Pharmaceutical Co., LTD, Tokyo (JP); Biomedical Research Group Inc., Tokyo (JP)

( * ) Notice: Subject to any disclaimer, the term of this patent is extended or adjusted under 35 U.S.C. 154(b) by 481 days.

(21) Appl. No.: 09/857,179

(22) PCT Filed: Oct. 18, 2000

(86) PCT No.: PCT/JP00/07216

§ 371 (c)(1),
(2), (4) Date: Jun. 19, 2001

(87) PCT Pub. No.: WO01/29207

PCT Pub. Date: Apr. 26, 2001

(30) Foreign Application Priority Data

Oct. 19, 1999 (JP) ............................................. 11-296817

(51) Int. Cl.[7] ........................ A61K 39/44; C07K 16/42; C12P 21/08; G01N 33/543; G01N 33/577
(52) U.S. Cl. ......................... 435/7.92; 435/6; 435/7.23; 435/7.4; 435/7.93; 435/70.21; 435/452; 435/333; 436/518; 436/548; 436/822; 530/388.21; 530/807
(58) Field of Search .............................. 435/67.23, 7.72, 435/7.73, 70.21, 452, 333; 436/518, 546, 822; 530/388.21, 807

(56) References Cited

FOREIGN PATENT DOCUMENTS

| JP | 62-299765 | 12/1987 |
| WO | WO 99/20748 | 4/1999 |

OTHER PUBLICATIONS

Honda et al., 2002. Development and characterization of a monoclonal antibody with cross–reactivity towards uracil and thymine, and its potential use in screening patients treated with 5–fluorouracil for possible risks. Clinica Chimia Acta 322: 59–66.*

Hellstrom et al., 1985. In Monoclonal Antibodies for Cancer Detection and Therapy (Baldwin et al., eds.) Academic Press, London, p. 20.*

Alarcon–Segovia et al., 1976. Immunochemical characterization of the anti–RNA antibodies found in scleroderma and systemic lupus erythematosus. II. Reactivity with HSA–coupled, uridine–containing, monophosphoric ribodinucleotides, Immunology 30: 413–41.*

Uhlig et al., 1989. Monoclonal autoantibodies derived from multiple sclerosis patients and control persons and their reactivities with antigens of the central nervous system. Autoimmunity 5: 87–99.*

(Continued)

Primary Examiner—Christopher L. Chin
Assistant Examiner—James L. Grun
(74) Attorney, Agent, or Firm—Oblon, Spivak, McClelland, Maier & Neustadt, P.C.

(57) ABSTRACT

A monoclonal antibody which reacts strongly with uracil and thymine but scarcely with N-carbamyl-β-alanine; a hybridoma producing this monoclonal antibody; a method of immunochemically assaying uracil or thymine characterized by using the above-described monoclonal antibody; and diagnostics for DPD deficiency containing the above monoclonal antibody. Because of high sensitivity and specific reaction with uracil and thymine, the above-described monoclonal antibody enables convenient, quick, and selective assaying of uracil and thymine in a sample. The antibody is useful in screening patients with DPD deficient cancer with contraindication to the administration of pyrimidine fluoride-based antitumor agents.

17 Claims, 2 Drawing Sheets

OTHER PUBLICATIONS

Y. Tsutsui, et al., Database Biosis 'Online!' Biosciences Information Service, 1 page, XP–002205201, "Immuno Fluorescent Detection of Thermolability of Chromatin In–Situ During the Cell Cycle Using Anti Thymine Antibodies", 1981.

D. Alarcon–Segovia, et al., The Lancet, vol. 15, pp. 363–365, XP–002915800, "Uracil–Specific Anti–R.N.A. Antibodies in Scleroderma", Feb. 15, 1975.

Anita A. Piper, et al., Biochimica et Biophysica Acta, vol. 633, pp. 400–409, "The Activities of Thymidine Metabolishing Enzymes During the Cell Cycle of a Human Lymphocyte Cell Line LAZ–07 Synchronised by Centrifugal Elutriation", 1980.

Albert H. Van Gennip, et al., Advances in Experimental Medicine and Biology, Purine and Pyrimidine Metabolism in Man VI, vol. 253A, pp. 111–118,"Comparative Study of Thymine and Uracil Metabolism in Healthy Persons and in a Patient with Dihydropyrimidine Dehydrogenase Deficiency", 1989.

Satoshi Sumi, et al., Journal of Chromatography B, vol. 672, pp. 233–239, "Automated Screening System for Purine and Pyrimidine Metabolism Disorders Using High–Performance Liquid Chromatography", 1995.

* cited by examiner

ANTIURACIL MONOCLONAL ANTIBODY

This application is a 35 U.S.C. 371 filing of PCT/JP00/07216 filed 18 Oct. 2000

TECHNICAL FIELD

The present invention relates to a monoclonal antibody useful for screening DPD-deficient cancer patients for whom administration of a pyrimidine fluoride-based antitumor agent is contraindicated; a hybridoma producing the monoclonal antibody; a method of immunochemically assaying uracil or thymine by use of the monoclonal antibody; and a diagnostic agent containing the monoclonal antibody for diagnosing DPD deficiency.

BACKGROUND ART

As antitumor agents, pyrimidine fluoride-based compounds such as fluorouracil are currently used. However, among cancer patients, some (approximately 3% of Caucasian breast cancer patients) are inherently deficient in dihydropyrimidine dehydrogenase (hereinafter abbreviated as DPD), which is an enzyme involved in the metabolism of the compound in its decomposition pathway. It has been reported that, when a pyrimidine fluoride-based antitumor agent is administered to such a DPD-deficient patient, the compound is not metabolized and remains in the body, leading to side effects or possibly even to death (*Biochim. Biophys. Acta* 633, 400–409(1980))

In an organism, uracil and thymine are generally metabolized into dihydrouracil and dihydrothymine, respectively, through the action of DPD. However, DPD-deficient patients are known to fail to metabolize uracil and thymine and to excrete large amounts of unchanged uracil and thymine into the blood or urine, particularly uracil (*Adv. Exp. Med. Biol.*, 253A, 111–118 (1989)). Accordingly, if uracil or thymine in blood or urine is assayed prior to administration of a pyrimidine fluoride-bases antitumor agent to cancer patients, DPD-deficient patients can be screened in advance. As a result, use of the antitumor agent can be discontinued or the dose of the agent can be reduced, to thereby avoid serious side effects.

Conventionally, methods for assaying uracil have been known, including a high-performance liquid chromatographic method (*Journal of Chromatography B*, 672 (1995), 233–239) and an immunoassay method making use of a monoclonal antibody for psuedouridine (Japanese Patent Publication (kokoku) 4-21479). However, the former method is disadvantageous in that the preparation of samples is cumbersome, imposes a heavy workload, and requires a significant level of skill. In addition, a long period of time is generally required for assaying a number of samples, and the high cost of measurement and other apparatuses make the method disadvantageous. In the latter method, the employed monoclonal antibody —an antibody used for diagnosing a progressive cancer —exhibits a reactivity with uracil of 30–40% and also a reactivity with pseudouridine as high as 95–99%. Thus, use of such a monoclonal antibody that has cross-reactivity with uracil and pseudouridine cannot distinguish DPD-deficient patients from non-deficient patients.

Under such circumstances, the present inventors previously found a monoclonal antibody which reacts strongly with uracil without cross-reacting with dihydrouracil—a metabolite of uracil in the organism—and with pseudouridine employed as a tumor marker (International Patent Publication WO 99/20748).

However, the above monoclonal antibody also reacts strongly with N-carbamyl-β-alanine, which is a metabolite of dihydrouracil and is contained in large amounts in normal urine, and has insufficient reactivity with uracil. Thus, use of the monoclonal antibody as a diagnostic agent for DPD deficiency is problematic.

Thus, an object of the present invention is to provide a monoclonal antibody having a higher specificity with uracil and thymine. Another object is to provide a hybridoma producing the monoclonal antibody. Still another object is to provide an immunochemical assay method which can correctly determine uracil and thymine contained in urine. Yet another object is to provide a diagnostic agent containing the monoclonal antibody for diagnosing DPD deficiency.

DISCLOSURE OF THE INVENTION

In view of the foregoing, the present inventors have carried out extensive studies on the relevant immunogen and immunization methods, and have found that a monoclonal antibody produced from a hybridoma which is formed by administering 5-bromo-1-carboxymethyluracil to an animal strongly reacts specifically with both uracil and thymine but exhibits no or low reactivity with pseudouridine, dihydrouracil, dihydrothymine, and N-carbamyl-β-alanine, and is therefore very useful for diagnosing DPD deficiency. The present invention has been accomplished on the basis of this finding.

Accordingly, the present invention provides a monoclonal antibody, characterized by reacting strongly with uracil and thymine but scarcely with N-carbamyl-β-alanine.

The present invention also provides a hybridoma producing the monoclonal antibody.

The present invention also provides a method for immunochemically assaying uracil and/or thymine by use of the monoclonal antibody.

The present invention also provides a diagnostic agent for diagnosing DPD deficiency, which agent contains the monoclonal antibody.

The present invention also provides a method for diagnosing DPD deficiency, characterized by assaying uracil and thymine in a specimen by use of the diagnostic agent.

The present invention also provides use of the monoclonal antibody for producing a diagnostic agent for diagnosing DPD deficiency.

The monoclonal antibody of the present invention reacts selectively with uracil and thymine at high sensitivity, to thereby selectively assay, rapidly and simply, uracil and thymine contained in a sample. In addition, the monoclonal antibody, exhibiting no or low reactivity with pseudouridine, dihydrouracil, and N-carbamyl-β-alanaine, is useful for diagnosing DPD deficiency by use of a human urine sample. Particularly, the monoclonal antibody is considerably useful for screening DPD-deficient cancer patients for whom administration of a pyrimidine fluoride-based antitumor agent is contraindicated.

BEST MODES FOR CARRYING OUT THE INVENTION

Figure 1:
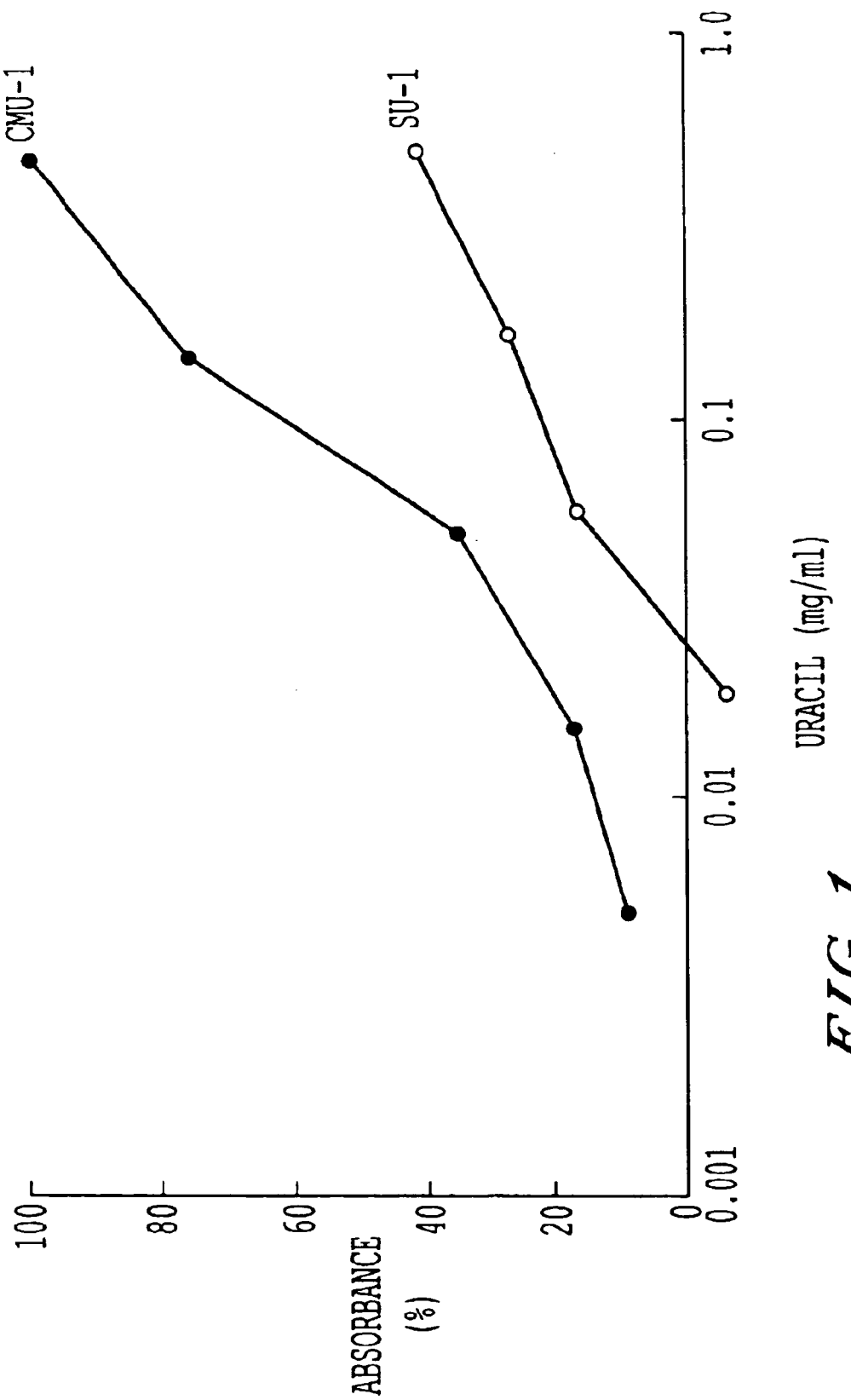
FIG. 1 is a graph showing reactivity with uracil for the monoclonal antibody of the present invention (CMU-1) and SU-1 studied through indirect competitive inhibition ELISA (Example 8).

The monoclonal antibody of the present invention reacts strongly with uracil and thymine but scarcely with N-carbamyl-β-alanine. The expression "scarcely with" refers to a state that the monoclonal antibody exhibits no dose-dependent response in connection with N-carbamyl-β-alanine.

Preferably, the monoclonal antibody of the present invention reacts strongly with uracil and thymine but scarcely with N-carbamyl-β-alanine, and exhibits no or low reactivity with pseudouridine, dihydrouracil, and dihydrothymine. The expression "no or low reactivity" refers to a state that no dose-dependent response is observed in connection with a specific compound concentration or to a state that a dose-dependent response is observed in connection with a specific compound concentration but affinity to the compound is low at a specific absorbance.

More specifically, the monoclonal antibody preferably exhibits a selectivity in cross reaction with N-carbamyl-β-alanine of 10% or less, when the selectivity in cross reaction with uracil or thymine is 90% or more. More preferably, when the selectivity in cross reaction with uracil or thymine is 90% or more, the monoclonal antibody exhibits a selectivity in cross reaction with N-carbamyl-β-alanine of 10% or less; a selectivity in cross reaction with pseudouridine of 33% or less; a selectivity in cross reaction with dihydrouracil of 8% or less; and a selectivity in cross reaction with dihydrothymine of 23% or less.

The globulin type of the monoclonal antibody of the present invention is not particularly limited, and any monoclonal antibody is acceptable so long as the antibody reacts strongly with uracil and/or thymine but scarcely with N-carbamyl-β-alanine. Specifically, any of IgG, IgM, IgA, IgE, and IgD is acceptable, with IgG and IgM being preferred.

No particular limitation is imposed on the cell strain which produces the monoclonal antibody of the present invention, so long as the produced antibody is endowed with the aforementioned characteristics. Examples of preferred cell strains include a hybridoma which is obtained through cell fusion of an antibody-producing cell with a myeloma cell strain.

As an antibody-producing cell for obtaining the monoclonal antibody of the present invention, there can be used a spleen cell, a lymphonodus cell, or a B-lymphocyte of an animal which is immunized in vivo with 5-halogeno-1-carboxymethyluracil serving as an immunogen. Examples of a halogen atom occupying the 5-position of 5-halogeno-1-carboxymethyluracil include fluorine, chlorine, bromine, and iodine, with a bromine atom being preferred.

The 5-halogeno-1-carboxymethyluracil per se has considerably weak immunogenicity. Thus, during immunization, the compound is preferably linked to an appropriate Schlepper, to thereby form an immunogen-Schlepper complex serving as an immunogen.

The term "Schlepper" refers to a carrier which links to a substance of very weak immunogenicity or to a substance, such as hapten, which per se has no antibody-productivity, to thereby potentiate or express immunogenicity. Generally, a protein of relatively high molecular weight is employed as a Schlepper. In addition to such a protein, cells such as erythrocyte and polysaccharide may also be used. Examples of the Schlepper include hemocyanine from SUKASHI-GAI (KLH), ovalbumin (OVA), bovine serum albumin (BSA), and rabbit serum albumin, with KLH and BSA being particularly preferred.

The method of linking 5-bromo-1-carboxymethyluracil and Schlepper is not particularly limited, and any known method can be employed. Examples include an acid anhydride mixture method (B. F. Erlanger et al., *J. Biol. Chem.* 234 1090–1094 (1954)) and an activation ester method (A. B. KARU et al., *J. Agric. Food. Chem.* 423–309 (1994)). There may also be employed, as a simple technique, a method employing an Immject Immunogen EDC Conjugation kit (product of Pierce) in accordance with the manual attached thereto.

Animals to be immunized include mice, rats, horses, goats, and rabbits, and an antigen is administered to these animals through a routine method. Specifically, an adjuvant such as complete Freund's adjuvant or incomplete Freund's adjuvant and the aforementioned 5-halogeno-1-carboxymethyluracil-KLH or 5-halogeno-1-carboxymethyluracil-BSA are mixed to prepare a suspension or emulsion thereof, and the suspension or emulsion is administered intravenously, subcutaneously, intradermally, intraperitoneally, or in a similar manner, into an animal, such as a mouse, several times so as to immunize the animal.

An antibody-producing cell such as a spleen cell is obtained from the thus-immunized animal and fused with a myeloma cell, to thereby produce a hybridoma according to the present invention.

Although the myeloma cell strains to be fused can be derived from mice, rats, horses, goats, rabbits or humans, preferably the cell strains are derived from the same animal from which an antibody-producing cell is obtained. For example, when an antibody-producing cell is derived from a mouse spleen cell, a counter myeloma cell strain obtained from a mouse is preferably used as the cell to be fused. Specifically, the myeloma cell strain is an 8-azaguanine-resistant mouse (BALB/c-derived) myeloma cell strain. Examples of specific cells include P3/X63-Ag8 (X63) [*Nature*, 256, 495–497 (1975)], P3/X63-Ag8.U1 (P3U1) [*Current Topics. in Microbiology and Immunology*, 81, 1–7 (1987)], P3/NSI-1Ag4-1 (NS-1) [*Eur. J. Immuno Meth.*, 35, 1–21 (1976)], Sp2/O-Ag14 (Sp2/O) [*Nature* 276, 269–270 (1978)], FO [*J. Immuno Meth.*, 35, 1–21 (1980)], MPC-11, X63.653, and S194, with P3U1 being preferred.

Cell fusion of an antibody-producing cell with a myeloma cell can be performed through any known method (e.g., see *Nature*, 256, 495–497 (1975), *Proc. Natl. Acad. Sci. USA* 78, 5122–5126 (1981)) or a method similar thereto. Specifically, the aforementioned antibody-producing cell and myeloma cell are fused in a conventionally employed nutrient medium in the presence of a fusion accelerator. The fusion accelerator is not particularly limited, and any of the typical accelerators, polyethylene glycol, Sendai virus, etc. can be used (e.g., Shuji YAMASHITA et al., Cell Tissue Chemistry, edited by Nihon Soshiki Saibo Kagaku-Kai; Gakusai Kikaku, 1986). Of these, polyethylene glycol is preferred in view of comparatively low cytotoxicity and ease of the fusion operation. In addition, an optional adjuvant such as dimethyl sulfoxide may be used in combination so as to enhance the fusion efficiency. Instead of the fusion method employing the aforementioned fusion accelerator, a fusion method through electric treatment (electric fusion) may appropriately be employed.

The number ratio of antibody-producing cells to myeloma cells may fall within the range employed in routine methods. Specifically, the antibody-producing cells may be used in an amount approximately 2–10 times, preferably 4–7 times, that of the myeloma cells.

A hybridoma group which has been endowed with the ability of antibody-production and proliferation, through cell fusion, of the antibody-producing cell and the myeloma cell can be selected through culturing by use of a customary medium for selection. Examples of the medium for selection include HAT medium when an 8-azaguanine-resistant strain is employed as the myeloma cell strain. The culturing in the HAT medium may be performed for a sufficient period of time such that unfused cells and the like, other than the target hybridoma, are extirpated, typically over 3–10 days.

Subsequently, the thus-obtained hybridoma is subjected to screening for strains producing a target anti-uracil monoclonal antibody and subsequent cloning, wherein the screening and cloning are carried out in accordance with a conventional method.

Screening strains which produce the anti-uracil monoclonal antibody of the present invention is performed by collecting a part of the culture supernatant containing the thus-obtained hybridoma group, to thereby prepare a sample, and detecting (confirming) uracil contained in the thus-collected sample through any of a variety of routine antibody-detection methods ("Hybridoma Method and Monoclonal Antibody," published by R&D Planning Co., Ltd., p. 30–53, Mar. 5, 1982); e.g., radioimmunoassay. Examples of the antibody-detection method include ELISA, a fluorescent antibody technique, a plaque method, a spot method, hemagglutination, and the Ouchterlony method. Of these, ELISA, particularly indirect competitive inhibition ELISA, is preferably employed, in view of sensitivity, speedy operation, accuracy, safety, and automation.

The hybridoma which has been proven, by screening, to produce a uracil-specific monoclonal antibody is cloned through a method in which a cell liquid is diluted through limiting dilution such that one hybridoma is included in one well (limiting dilution); a method in which the cell liquid is spread onto a soft agar medium and the formed colony is collected; a method in which one cell is taken by means of a micromanipulator; or a method in which one cell is separated by means of a cell-sorter (sorter cloning).

As the cloning method, limiting dilution is preferably employed, in view of ease of operation. Specifically, wells containing a hybridoma for which antibody titer has been confirmed are subjected to limiting dilution 1–4 times, and the hybridoma for which antibody titer has been constantly confirmed is selected as a cell strain producing an anti-uracil monoclonal antibody.

The hybridoma of the present invention obtained through the aforementioned method may be stored by freezing at −80° C. or lower (e.g., −195° C. in liquid nitrogen) in a culture medium; e.g., RPMI 1640 medium containing 10% fetal bovine serum and including $5 \times 10^6$ cells/mL or more, with optional 10% dimethyl sulfoxide serving as a freeze stabilizing agent.

As further mentioned, the hybridoma of the present invention is stable during culture in a basal medium such as RPMI 1640, DMEM, or IMEM and produces and secretes a monoclonal antibody which reacts specifically with both uracil and thymine but exhibits low or scarce reactivity with pseudouridine, dihydrouracil, dihydrothymine, and N-carbamyl-β-alanine. In addition, the hybridoma, stabilized in nitrogen liquid, can be stored therein and can be readily reclaimed therefrom. The hybridoma of the present invention (mouse hybridoma CMU-1) is useful as a readily available source for producing a genuine monoclonal antibody reacting with a uracil antigen, and is deposited as "FERM BP-6870" (date of deposition: 1999/9/7) with the National Institute of Bioscience and Human-Technology, Agency of Industrial Science and Technology, Ministry of International Trade and Industry (address: 1–3, Higashi 1-chome, Tsukuba-shi, Ibaraki-ken 305-8566 JAPAN) under the Budapest Treaty.

The target monoclonal antibody is produced from the thus-obtained hybridoma by culturing the hybridoma in a routine manner such as cell culture or formation from ascites; separating the monoclonal antibody from the culture supernatant or the ascites; and purifying. The monoclonal antibody obtained from the culture supernatant or ascites can be purified through a routine method. Specifically, methods such as fractionating by use of ammonium sulfate, gel filtration, ion-exchange chromatography, and affinity chromatography may appropriately be applied in combination.

The thus-obtained monoclonal antibody of the present invention can be evaluated in terms of selectivity in cross-reaction, through a method such as indirect competitive inhibition ELISA as described in the Examples shown below. In the Examples, the monoclonal antibody has been proven to react specifically with both uracil and thymine and to exhibit low or scarce reactivity with pseudouridine, dihydrouracil, dihydrothymine, and N-carbamyl-β-alanine; i.e., has been proven to have high reactivity with uracil and thymine and high reaction specificity thereto.

Thus, the monoclonal antibody of the present invention has high reactivity with both uracil and thymine but exhibits low or scarce reactivity with pseudouridine, dihydrouracil, dihydrothymine, and N-carbamyl-β-alanine. In addition, the antibody can be supplied constantly and in a large amount by culturing the hybridoma of the present invention. Therefore, the antibody is useful as a reagent for specifically assaying uracil and thymine immunochemically and can be used for purifying uracil and thymine.

As described above, the monoclonal antibody of the present invention has reaction specificity; i.e., low or scarce reactivity with pseudouridine, dihydrouracil, dihydrothymine, and N-carbamyl-β-alanine, which are substances that possibly migrate into the urine of cancer patients. Thus, the monoclonal antibody of the present invention is useful for screening DPD-deficient patients excreting uracil and thymine into the urine as a result of DPD deficiency and DPD-non-deficient patients, particularly for cancer patients.

No particular limitation is imposed on the method for immunochemically assaying uracil and thymine by use of the monoclonal antibody of the present invention, so long as the method can specifically detect or determine uracil and thymine in a sample possibly containing uracil and thymine. However, a preferred assay method includes a step of incubating a biological sample of a patient and the monoclonal antibody of the present invention under the conditions for forming an antigen-antibody complex, and a step of detecting the formed antigen-antibody complex. The above assay method may be varied in accordance with techniques that are typically employed in the art relating to the present invention, and examples of the variations include direct, indirect, competitive, and sandwich methods. Specific examples include ELISA, radioimmunoassay, a fluorescent antibody technique, and an emission antibody technique, with ELISA being preferred.

In one example, immobilized ELISA of a human urine sample can be performed in the following manner:

(a) immobilizing the monoclonal antibody of the present invention onto an arbitrary carrier, and covering, with a protein irrelevant to the antigen, a part of the solid surface that is not covered with the antibody;

(b) washing the surface and adding the urine sample to be assayed and an enzyme-labeled antigen; e.g., enzyme-labeled (5-halogeno-1-carboxymethyluracil)-Schlepper complex so as to cause a competitive reaction; and (c) adding an enzyme substrate thereto and measuring the decrease in absorbance attributable to addition of the sample to be assayed. Briefly, detection of the decrease in absorbance attributable to addition of the sample to be tested can determine the presence of uracil in the urine sample, and measuring the amount of the decrease in absorption attributable to addition of the sample to be tested can quantitatively determine uracil and thymine in the urine sample, by use of a calibration curve established in advance from data on predetermined amounts of uracil and thymine.

Indirect competitive inhibition ELISA by use of the monoclonal antibody of the present invention can assay uracil or thymine in a sample within a range of 0.001–2 mg/mL, preferably 0.005–0.5 mg/mL. Assaying uracil or thymine in a urine sample through indirect competitive inhibition ELISA can be performed in the following manner.

(a) causing a (5-halogeno-1-carboxymethyluracil)-Schlepper complex serving as an antigen to adsorb onto a carrier, to thereby immobilize the antigen;

(b) blocking a portion of the carrier surface other than the antigen-adsorbed portion with a protein irrelevant to the antigen;

(c) adding a urine sample to be tested and the monoclonal antibody of the present invention so as to bind the monoclonal antibody with the immobilized antigen and free uracil (or thymine) in a competitive manner, thereby forming an immobilized antigen-antibody complex and a free uracil (or thymine)-antibody complex;

(d) washing off the free uracil (or thymine)-antibody complex and reacting an enzyme-labeled secondary antibody with the immobilized antigen-antibody complex; and (e) reacting an appropriate substrate with the enzyme and measuring absorbance.

In the aforementioned step (a), the aforementioned immunogens can be utilized as the (5-halogeno-1-carboxymethyluracil)-Schlepper complex serving as an immobilized antigen. Basically, the same immunogen as used to prepare an antibody-producing cell is preferably employed as the immobilized antigen. However, the 5-halogeno-1-carboxymethyluracil-Schlepper complex serving as the immobilized antigen is not necessarily identical with the same complex serving as the immunogen. Briefly, 5-halogeno-1-carboxymethyluracil-BSA complex can serve as the immunogen and 5-halogeno-1-carboxymethyluracil-KLH can serve as the immobilized antigen.

No particular limitation is imposed on the carrier onto which the antigen is immobilized, and any carrier which is typically used in ELISA can be used. Examples of the carrier include a microplate or beads formed of polystyrene or polyvinyl resin, with a 96-well microplate being preferred. The concentration of the antigen is not particularly limited and is appropriately predetermined generally within a wide range of approximately 0.01–100 $\mu$g/mL, preferably 0.4–50 $\mu$g/mL. When a 96-well microplate is used as a carrier, the antigen may be used in a volume sufficient to cover the bottom surfaces of the wells in their entirety. Generally, a volume of approximately 20–100 $\mu$L per well is preferably used.

No particular limitation is imposed on the adsorption conditions. Typically, allowing to stand at approximately 4–40° C. for approximately one hour to one night is suitable, and allowing to stand at approximately 4° C. for approximately one night or at approximately 37° C. for approximately two hours is preferred.

In step (b), examples of proteins which can be used for blocking include calf serum, ovalbumin, bovine serum albumin, fetal calf serum, skim milk, and gelatin, with gelatin and calf serum being preferred. No particular limitation is imposed on the blocking conditions, and typically, allowing to stand at approximately 4–40° C. for approximately one hour to one night is suitable, and allowing to stand at approximately 4° C. for approximately one night or at approximately 37° C. for approximately two hours is preferred. After completion of blocking, the microplate is washed by use of a buffer. The buffer used herein is not particularly limited, and, for example, phosphate buffered saline (PBS) containing Tween 20 (pH 7.3–7.7) is preferred.

In step (c), no particular limitation is imposed on the specific conditions, and typically, allowing to stand at approximately room temperature to 40° C. for approximately 0.5–3 hours is suitable, and allowing to stand at approximately 37° C. for approximately one hour is preferred. After completion of reaction, the microplate is washed by use of a buffer. The buffer herein used is not particularly limited, and, for example, PBS containing Tween 20 (pH 7.3–7.7) is preferred.

As the secondary antibody used in step (d), an enzyme-labeled anti-mouse immunoglobulin antibody can be used. Examples of the enzyme include alkaline phosphatase (AP), horse radish peroxidase (HRPO), $\beta$-galactosidase ($\beta$-GS), glucose oxidase (GO), and urease. Among such secondary antibodies, an AP-labeled anti-mouse immunoglobulin antibody is preferred. The secondary antibody is typically diluted for use, and there is preferably used a secondary antibody which has been diluted at a dilution factor of approximately 100–10,000 times, more preferably approximately 200–1,000 times, based on the concentration of the monoclonal antibody (primary antibody) which has been bound with the microplate via the uracil-Schlepper complex. In order to dilute the secondary antibody, a protein used for blocking that is diluted with PBS; e.g., PBS (pH 7.3–7.7) containing 0.1% gelatin, is preferably used. The reaction conditions are not particularly limited, and the reaction is typically carried out at approximately 37° C. for approximately one hour. After completion of the reaction, the reaction system is washed with a buffer. Through the above reaction, the secondary antibody is caused to bind with the monoclonal antibody which is bound with the microplate via the immobilized antigen.

In step (e), a substrate is reacted with the enzyme bound to the secondary antibody so as to allow the substrate to develop color. In the reaction system, an optional color developer may further be added. The change in absorbance is measured. More specifically, in a preferred method, when alkaline phosphatase is employed as the labeling enzyme to be bound with the secondary antibody, p-nitrophenylphosphoric acid is employed as a substrate, to thereby develop color through enzymatic reaction. The enzymatic reaction is terminated through addition of 2N NaOH, and absorbance is measured at 415 nm.

In the case in which peroxidase is employed as the labeling enzyme to be bound with the secondary antibody, hydrogen peroxide and o-phenylenediamine are preferably employed as a substrate and a color developer, respectively. In this case, specific conditions are not particularly limited, and there is used a method in which a solution of a color developer is added to a reaction system; the system is allowed to react at approximately 25° C. for approximately 10 minutes; and the enzymatic reaction is terminated through addition of 4N sulfuric acid.

When o-phenylenediamine is employed as a color developer, the absorbance at 492 nm is measured. In addition, sensitizing by use of an avidin-biotin system may also be employed.

In a simple manner for carrying out the aforementioned immunochemical assay, a diagnostic agent for diagnosing DPD deficiency that contains the antiuracil monoclonal antibody of the present invention is used.

Specifically, the diagnostic agent used—for detecting or quantitating uracil or thymine in a sample to be assayed—is a kit containing the monoclonal antibody of the present invention and optional uracil or 5-halogeno-1-carboxymethyluracil-Schlepper complex.

The diagnostic agent may be a set containing, in addition to the monoclonal antibody of the present invention, at least one to five ingredients selected from among carriers for immobilization, labeling agents, substrates (detection agents) corresponding to the labeling agents, antigens, and secondary antibodies (e.g., anti-mouse immunoglobulin). When the set contains a labeling agent, the labeling agent may be conjugated in advance with an arbitrary ingredient such as a secondary antibody. Examples of the labeling agent include a variety of compounds such as radioisotopes, enzymes, and fluorescent substances. Of these, enzymes are preferred from a variety of viewpoints, such as operability.

The diagnostic agent may further contain, for measurement purposes, appropriate ingredients such as a diluent for an antibody or an antigen, a diluent for reaction, a buffer, a detergent, a substrate-dissolving agent, a reaction-terminating agent, and a solid-adsorption-preventing agent.

EXAMPLE 1

Preparation of 5-bromo-1-carboxymethyluracil-Schlepper Complex

By use of an Immject Immunogen EDC Conjugation kit (product of Pierce) and in accordance with the manual attached thereto, 5-bromo-1-carboxymethyluracil was bound to bovine serum albumin (BSA) or hemocyanin (KLH), to thereby prepare a 5-bromo-1-carboxymethyluracil-BSA complex or a 5-bromo-1-carboxymethyluracil-KLH complex. Specifically, the following method was employed.

1) 5-Bromo-1-carboxymethyluracil (4 mg) was dissolved in a conjugation buffer (1 mL; 0.1 M MES (2-(N-Morpholino)-ethane sulfonic acid), 0.9 M NaCl, 0.02%, $NaN_3$, pH 4.7).

2) BSA (or KLH) (10 mg) was dissolved in another portion of the conjugation buffer (1 mL).

3) The 5-bromo-1-carboxymethyluracil solution (50 $\mu$L) prepared in step 1) and 1-ethyl-3-(3-dimethyl-aminopropyl) carbodiimide (EDC) (125 $\mu$L; when KLH is used in place of BSA, 50 $\mu$L) were added to the BSA (or KLH) solution (200 $\mu$L) prepared in step 2).

4) The solution prepared in step 3) was allowed to stand at 37° C. for 2 hours, and subjected to centrifugation at 10,000 rpm for 5 minutes, to thereby remove pellets.

5) The solution obtained in step 4) was added to a D-salt dextran desalting column, and the eluate was fractionated at 0.5 mL/tube. The absorbance of each fraction was measured at 280 nm and 260 nm. The fractions corresponding to the first peak were collected, to thereby obtain a solution of 5-bromo-1-carboxymethyluracil-BSA (or KLH) complex.

6) The presence of the complex was confirmed through analysis of absorbance in the vicinity of OD 260 nm, which is attributed to the pyrimidine skeletal structure of 5-bromo-1-carboxymethyluracil. As a result, in relation to the 5-bromo-1-carboxymethyluracil-BSA complex, it was deduced that 7.31 molecules of 5-bromo-1-carboxymethyluracil had been bound to one BSA molecule, whereas in relation to the 5-bromo-1-carboxymethyluracil-KLH complex, it was deduced that 26 molecules of 5-bromo-1-carboxymethyluracil had been bound to one KLH molecule.

The above-described complexes can be utilized to prepare a hybridoma and a monoclonal antibody.

EXAMPLE 2

Preparation of Antibody-Producing Cells

To each of five BALB/c mice, complete Freund's adjuvant (200 $\mu$L) containing the antigen prepared in Example 1 (5-bromo-1-carboxyluracil-KLH, 10 $\mu$g) was injected intraperitoneally. Two weeks thereafter, incomplete Freund's adjuvant (200 $\mu$L) containing the same antigen (10 $\mu$g) was intraperitoneally administered to the same mice.

A further 2 weeks thereafter, blood was drawn from the fundus of the mice. While the thus-collected blood was used as an antibody source, inhibition of antigen-antibody reaction by uracil was checked. PBS solution (200 $\mu$L) containing the antigen (10 $\mu$g) was administered intravenously to a mouse whose serum showed the highest level of inhibition by uracil. Three days thereafter, the spleen of the mouse was aseptically removed, and washed with RPMI1640 medium twice. The spleen was transferred to a clean bench, and washed with the same medium two additional times. Subsequently, the spleen was minced in a Petri dish, and the thus-obtained spleen cells were suspended in RPMI1640 medium. The cell suspension was placed in a 15-mL centrifuge tube and subjected to centrifugation for 7 minutes at 1,000 rpm at room temperature. The supernatant was discarded.

The cell sediments were suspended in RPMI1640 medium (10 mL), and the resultant cell suspension was allowed to stand for 3 minutes at room temperature. The cell suspension was withdrawn to a 50-mL centrifuge tube so as not to carry the tissue mass at the bottom of the centrifuge tube, and subjected to centrifugation for 7 minutes at 1,000 rpm at room temperature. The supernatant was discarded, and RPMI1640 medium was added to the centrifuge tube such that the total volume of the suspension became 10 mL. The number of spleen cells having a nucleus was counted with a hemocytometer. The spleen cells prepared through the above-described procedure were used for fusion with myeloma cells.

EXAMPLE 3

Cell Fusion (1) Preparation of Myeloma Cells

P3U1 cells of 8-azaguanine-resistant mouse (BALB/c mouse) myeloma strain were used for cell fusion with the aforementioned spleen cells. The P3U1 cells had been subcultured in advance with RPMI1640 medium supplemented with 10% fetal bovine serum (FBS).

The P3U1 cells of day 1 subculture were transferred into a 50-mL centrifuge tube, and subjected to centrifugation for 5 minutes at 1,000 rpm at room temperature. The supernatant was discarded, and the P3U1 cells were suspended in RPMI1640 medium (10 mL). The number of cells was counted with a hemocytometer. The thus-prepared myeloma cells (P3U1 cells) were used for cell fusion.

(2) Cell Fusion

The number of cells of the P3U1 cells prepared in step (1) and that of the sensitized cells prepared in Example 2 were counted, and the cells were mixed at the following ratio (by number of cells). P3U1 cells : sensitized cells=1 : 5. The mixture was allowed to stand for 10 minutes at room temperature, followed by centrifugation for 5 minutes at 1,000 rpm at room temperature. The supernatant was discarded, and the cell pellet was loosened by tapping the centrifuge tube. 50% Polyethylene glycol (average molecular weight=1,000) was added, over 10 seconds, to the centrifuge tube containing the loosened cells in an amount of 1 mL per combined cell count of $2\times10^8$ cells while spinning the centrifuge tube. Spinning was continued for a further 50 seconds. Subsequently, while spinning, RPMI1640 medium (15 mL) was added over 3 minutes, and an additional 25 mL of the medium was added over 1 minute. The contents of the centrifuge tube were made uniform through gentle pipetting, followed by centrifugation for 5 minutes at 1,000 rpm at room temperature. The supernatant was discarded, and the pellet was suspended in HAT medium supplemented with 10% fetal bovine serum (to make the concentration of the sensitized cells $1.6\times10^8$ cells/mL). The thus-prepared cell suspension was plated in a 96-well flat-bottomed plate at 200–250 μL/well. The cells were incubated for a period of 10 to 14 days at 37° C. under 5% $CO_2$.

EXAMPLE 4

Screening of Hybridoma

The hybridoma cells obtained in Example 3 were subjected to a screening test through ELISA.

Into a 96-well immunoplate, uracil-BSA complex (10 μg/mL as reduced to BSA) was placed at 50 μL/well, and allowed to stand overnight at 4° C. Subsequently, the immunoplate was washed 7 times with PBS containing 0.1% polyoxyethylene(20) sorbitan monolaurate (product of Wako Pure Chemical Industries, Ltd.; a product equivalent to Tween 20) (pH 7.3–7.7, product of Nissui Chemical; hereinafter referred to as PBS-T). Subsequently, 0.2% gelatin (200 μL) was added to each well, and the immunoplate was left for 2 hours at 37° C., or overnight at 4° C.

Subsequently, the immunoplate was washed five times with PBS-T, and one of the below-described samples (50 μL/well) was added to the immunoplate, which was then left for 1 hour at 37° C.

(i) a reaction mixture prepared by mixing the supernatant of the hybridoma culture obtained in Example 3 (hereinafter referred to as the hybridoma culture supernatant) (30 μL) and PBS (30 μL) for reaction at 37° C. for one hour;

a (ii) a reaction mixture obtained by mixing the hybridoma culture supernatant (30 μL) and a solution (30 μL) of uracil in PBS (uracil concentration: 1 mg/mL) for reaction at 37° C. for one hour; and (iii) 1 μg/mL healthy mouse IgG (product of Biological). Subsequently, the wells were washed five times with PBS-T, and to each well was added alkaline-phosphatase-labeled (AP-labeled) anti-mouse-multivalent-immunoglobulin antibody (product of Sigma), which had been 1,000-fold diluted with 0.1% gelatin, (50 μL). Subsequently, the mixture was allowed to stand for one hour at 37° C. Subsequently, the wells were washed five times with PBS-T. A solution of disodium p-nitrophenylphosphate (product of Wako Chemical Industries, Ltd.) dissolved in substrate buffer (1 mg/mL) was added to each well (100 μL/well), and left for 30 minutes at 37° C. To the reaction mixtures, 2N NAOH (50 μL/well) was added and then mixed by use of a platemixer, to thereby stop the reaction. Absorbance at 415 nm was measured by use of a microplate reader.

The percent absorption was calculated by use of the following equation:

$$\text{Percent Absorption}(\%) = \left(1 - \frac{OD_{uracil} - OD_{control}}{OD_{PBS} - OD_{control}}\right) \times 100$$

wherein, $OD_{PBS}$: Absorbance measured by means of ELISA for a sample in which the hybridoma culture supernatant had been pre-treated only with PBS), $OD_{uracil}$: Absorbance measured by means of ELISA for a sample in which the hybridoma culture supernatant had been pre-treated with uracil in PBS), and $OD_{control}$: Absorbance measured in ELISA of a sample treated only with heal thy mouse IgG).

EXAMPLE 5

Cloning

The monoclonal-antibody-producing hybridoma obtained in Example 4 was cloned twice through a known customary limiting dilution method.

Specifically, the number of the monoclonal-antibody-producing hybridoma cells obtained in Example 4 was counted. A hybridoma cell and RPMI1640 (0.2 mL) containing 10% FBS and 10% BM condimed H1 (Registered Trademark of Boehringer Mannheim) were placed into each well of an immunoplate, and incubated under 5% $CO_2$ at 37° C. for 10–14 days.

The resultant hybridoma clones were subjected to screening through ELISA as described in Example 4. Subsequently, the selected hybridoma clones were cloned again through the above-described method, followed by screening through the aforementioned ELISA again. As a result, the cloned cells (2D3 and 2H10) which produce an antibody specific to uracil and thymine were screened out from the monoclonal-antibody-producing hybridomas. One of the thus-obtained cloned cells (2D3), mouse hybridoma CMU-1, was deposited with the National Institute of Bioscience and Human-Technology, Agency of Industrial Science and Technology, Ministry of International Trade and Industry under the Budapest Treaty, (accession No.: FERM BP-6870).

EXAMPLE 6

Storage of Anti-Uracil-Monoclonal-Antibody-Producing Hybridomas

The monoclonal-antibody-producing hybridoma clones obtained in Example 5 were added to RPMI1640 medium containing 10% FBS and 10% DMSO so that the hybridoma concentration became $1\times10^7$ cells/mL. Aliquots (1 mL) of the resultant mixture were placed in CryoTubes (product of Nunc), followed by freezing in a deep freezer at −90° C., and storing in liquid nitrogen.

EXAMPLE 7

Preparation of Monoclonal Antibody and its Evaluation

The monoclonal-antibody-producing hybridoma, mouse hybridoma CMU-1, obtained in Example 5 was cultured in RPMI1640 medium containing 10% FBS and 10% BM condimed H1 (product of Boehringer Mannheim) under 5% $CO_2$ at 37° C. for 2–3 days.

By use of the hybridoma culture supernatant obtained from the above-described incubation, the reactivity of the monoclonal antibody, CMU-1, of the present invention was studied through the indirect competitive inhibition ELISA described in Example 4.

Specifically, an aliquot (50 µL) of uracil-BSA complex (10 µg/mL) was placed in each well of a 96-well immunoplate (Immunoplate I, product of Nunc), and allowed to stand overnight at 4° C. Each well was washed five times with PBS-T (200 µL) containing 0.1% Tween 20. Subsequently, to each well of the immunoplate, PBS (200 µL) containing 0.2% gelatin serving as a blocking agent was added, and the mixture was allowed to stand overnight at 4° C. Each well was again washed five times with PBS-T, to thereby prepare a plate.

Meanwhile, each of the follow samples:

(i) a mixture of the aforementioned hybridoma culture supernatant (30 µL) and PBS (30 µL);

(ii) a reaction mixture obtained by mixing the hybridoma culture supernatant (30 µL) and PBS (30 µL) containing uracil at a concentration of 0.03–1.0 mg/mL and causing reaction to proceed at 37° C. for one hour; and (iii) 1 µL/mL healthy mouse IgG (product of Biologicals) was added to a 96-well plate to which the above antigen had been adsorbed (50 µL/well), and the plate was left to stand for one hour at 37° C. Subsequently, the plate was washed five times with PBS-T, and to each well, aliquots (50 µL) of AP-labeled anti-mouse antibody (serving as the second antibody, product of Sigma), which had been 1,000-fold diluted with PBS containing 0.1% gelatin, were added, and the mixtures were allowed to stand for one hour at 37° C. Subsequently, each well was washed five times with PBS-T. An enzyme substrate buffer solution (p-nitrophenylphosphate, 1 mg/mL, pH 9.8) was added to each well (100 µl/well), and left to stand for 30 minutes at 37° C. To the reaction mixtures, 2N NaOH (50 mL/well) was added, to thereby stop the reaction. Absorbance at 415 nm was measured by use of a microplate reader. For comparison, the same procedure was independently performed on hybridoma FERM BP-6141 described in PCT publication No. WO99/20748. The results are shown in FIG. 1. The percent absorption was calculated from the above-described equation.

As shown in FIG. 1, the monoclonal antibody of the present invention enables detection of uracil in a concentration range of 0.005–0.5 mg/mL. The detection sensitivity for uracil detection is considerably enhanced as compared with monoclonal antibody SU-1 originating from hybridoma FERM BP-6141.

EXAMPLE 8

Cross Reactivity Test

In a manner similar to that of Example 7, reactivity of the monoclonal antibody of the present invention with other compounds was investigated. Specifically, the procedure of step (ii) of Example 7 for investigating inhibition with uracil was repeated, except that pseudouridine, dihydrouracil, dihydrothymine, thymine, cytosine, or N-carbamyl-β-alanine (1 mg/mL) was used instead of uracil (1 mg/mL), to thereby investigate reactivity of the monoclonal antibody of the present invention with uracil compounds. As a comparative antibody, a monoclonal antibody (SU-1) derived from hybridoma "FERM BP-6141" described in WO 99/20748 was used. Table 1 shows the results.

TABLE 1

| | Monoclonal antibody | |
|---|---|---|
| Compound* | Present invention (CMU-1) | Comparative (SU-1) |
| Uracil | 95–96% | 41% |
| Thymine | 91–97% | 5% |
| N-Carbamyl-β-alanine | 8% | 91% |
| Dihydrouracil | 8% | 2% |
| Dihydrothymine | 22% | — |
| Pseudouridine | 32% | 26% |
| Cytosine | 15% | 15% |

*Final concentration 0.5 mg/mL

As shown in Table 1, the monoclonal antibody of the present invention reacted strongly with uracil and thymine and exhibited dose-dependent response. However, reactivity thereof with N-carbamyl-β-alanine, dihydrouracil, dihydrothymine, pseudouridine, and cytosine was found to be low. In contrast, the comparative antibody exhibited higher reactivity with N-carbamy-β-alanine than with uracil or thymine.

Figure 2:
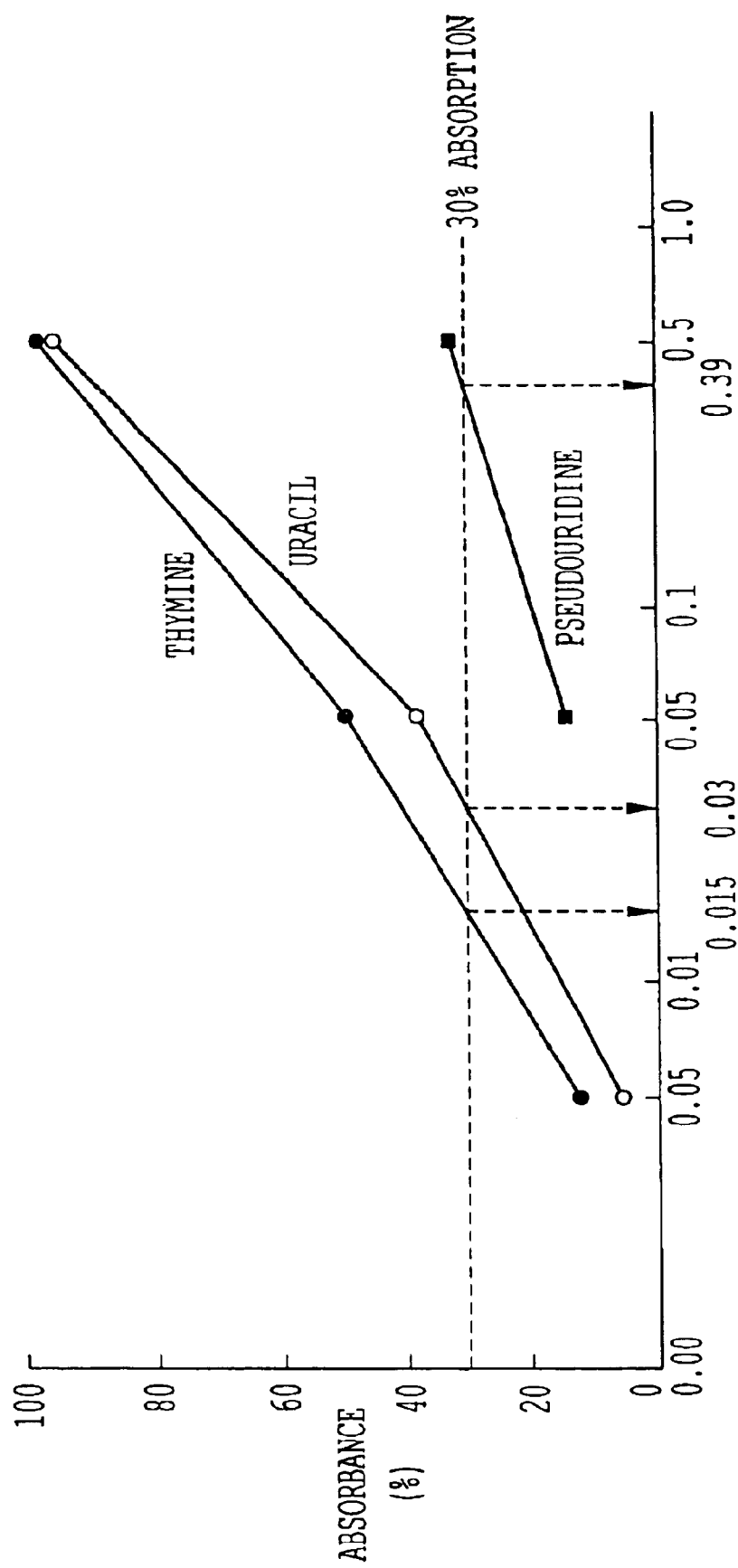
FIG. 2 is a graph showing the relationship between the percent absorption of the color-developed monoclonal antibody of the present invention and the concentrations of uracil, thymine, and pseudouridine.

In addition, the antibody of the present invention exhibited no dose-dependent response to N-carbamyl-β-alanine, dihydrouracil, dihydrothymine, and cytosine, but did exhibit dose-dependent response to pseudouridine. Thus, the concentration-percent absorption relationship in terms of uracil, thymine, and pseudouridine to which dose-dependent response had been confirmed was investigated. FIG. 2 shows the results, and Table 2 shows the concentrations (mg/mL) of respective compounds when the percent absorption reached 30% ($ED_{30}$)

TABLE 2

| Compound | $ED_{30}$ (mg/mL) |
|---|---|
| Uracil | 0.03 |
| Thymine | 0.015 |
| Pseudouridine | 0.39 |

The results indicated that the concentration of uracil was 1/13 that of pseudouridine so as to exhibit the same percent absorption and that the concentration of thymine was 1/26 that of pseudouridine so as to exhibit the same percent absorption. Accordingly, the binding ability of uracil was found to be 13 times that of pseudouridine and the binding ability of thymine was found to be 26 times that of pseudouridine.

INDUSTRIAL APPLICABILITY

The monoclonal antibody of the present invention is able to selectively assay, at high speed and in a simple manner, uracil and thymine contained in a sample. In addition, the monoclonal antibody is useful for diagnosing DPD deficiency by use of a human urine sample. Particularly, the monoclonal antibody is considerably useful for screening DPD-deficient cancer patients with contraindication to the administration of a pyrimidine fluoride-based antitumor agent.

What is claimed is:

1. A monoclonal antibody, which exhibits a selectivity in cross reaction with N-carbamyl-β-alanine of 10% or less, when the selectivity in cross reaction with each of uracil and thymine is 90% or more.

2. A hybridoma producing the monoclonal antibody of claim 1.

3. The monoclonal antibody of claim 1, which is produced from a hybridoma which is formed from a myeloma cell and an antibody-producing cell derived from an animal to which 5-halogeno-1carboxymethyluracil linked to a carrier has been administered.

4. A composition, comprising the monoclonal antibody of claim 1; and a carrier.

5. The monoclonal antibody of claim 1, which exhibits low reactivity with pseudouridine, dihydrouracil, and dihydrothymine.

6. A method for immunochemically assaying uracil and thymine comprising contacting a sample possibly containing uracil and thymine with the monoclonal antibody of claim 1; and detecting a formed antibody-antigen complex, wherein the presence of the antibody-antigen complex is indicative of the presence of uracil and thymine in the sample.

7. A method for diagnosing dihydropyrimidine dehydrogenase (DPD) deficiency in an individual, comprising, assaying uracil and thymine according to the method of claim 6, wherein the sample is obtained from the individual and wherein an increase of uracil and thymine in the sample relative to a sample obtained from an individual that is not DPD deficient is diagnostic for DPD deficiency in the individual.

8. The monoclonal antibody as described in claim 3, wherein the hybridoma is FERM BP-6870.

9. A hybridoma producing the monoclonal antibody of claim 8.

10. A composition, comprising the monoclonal antibody of claim 8; and a carrier.

11. A method for immunochemically assaying uracil and thymine comprising contacting a sample possibly containing uracil and thymine with the monoclonal antibody of claim 8; and detecting a formed antibody-antigen complex, wherein a detected antibody-antigen complex is indicative of the presence of uracil and thymine in the sample.

12. A method for diagnosing dihydropyrimidine dehydrogenase (DPD) deficiency in an individual, comprising, assaying uracil and thymine according to the method of claim 11, wherein the sample is obtained from the individual and wherein an increase of uracil and thymine in the sample relative to a sample obtained from an individual that is not DPD deficient is diagnostic for DPD deficiency in the individual.

13. The monoclonal antibody of claim 1, which exhibits a selectivity in cross reaction with N-carbamyl-β-alanine of 10% or less; a selectivity in cross reaction with pseudouridine of 33% or less; a selectivity in cross reaction with dihydrouracil of 8% or less; and a selectivity in cross reaction with dihydrothymine of 23% or less; when the selectivity in cross reaction with each of uracil and thymine is 90% or more.

14. A hybridoma producing the monoclonal antibody of claim 13.

15. A composition, comprising the monoclonal antibody of claim 13, and a carrier.

16. A method for immunochemically assaying uracil and thymine comprising contacting a sample possibly containing uracil and thymine with the monoclonal antibody of claim 13; and detecting a formed antibody-antigen complex, wherein a detected antibody-antigen complex is indicative of the presence of uracil and thymine in the sample.

17. A method for diagnosing dihydropyrimidine dehydrogenase (DPD) deficiency in an individual, comprising, assaying uracil and thymine according to the method of claim 13, wherein the sample is obtained from the individual and wherein an increase of uracil and thymine in the sample relative to a sample obtained from an individual that is not DPD deficient is diagnostic for DPD deficiency in the individual.

* * * * *